(12) United States Patent
Viart et al.

(10) Patent No.: US 9,743,962 B2
(45) Date of Patent: Aug. 29, 2017

(54) GRIPPING DEVICE FOR A PEDICLE SCREW

(71) Applicant: CLARIANCE, Beaurains (FR)

(72) Inventors: Guy Viart, Saint Leger (FR); Brice Krier, Dainville (FR); Jean Yves Leroy, Capagne-les-Hesdin (FR); Nicolas Virgaux, Paris (FR); Jean Paul Steib, Strasbourg (FR); Sebastien Schuller, Strasbourg (FR)

(73) Assignee: CLARIANCE, Beaurains (FR)

( * ) Notice: Subject to any disclaimer, the term of this patent is extended or adjusted under 35 U.S.C. 154(b) by 0 days.

(21) Appl. No.: 15/223,251

(22) Filed: Jul. 29, 2016

(65) Prior Publication Data

US 2017/0027612 A1 Feb. 2, 2017

Related U.S. Application Data

(60) Provisional application No. 62/199,320, filed on Jul. 31, 2015.

(51) Int. Cl.
*A61B 17/70* (2006.01)

(52) U.S. Cl.
CPC ........ *A61B 17/708* (2013.01); *A61B 17/7082* (2013.01)

(58) Field of Classification Search
CPC ............ A61B 17/7091; A61B 17/7074; A61B 17/7079; A61B 17/7086
See application file for complete search history.

(56) References Cited

U.S. PATENT DOCUMENTS

| 2004/0049191 | A1 | 3/2004 | Markworth et al. |
| 2011/0263945 | A1* | 10/2011 | Peterson ............ A61B 17/0218 600/213 |

FOREIGN PATENT DOCUMENTS

WO  2008/039441 A1  4/2008

* cited by examiner

*Primary Examiner* — Christopher Beccia
(74) *Attorney, Agent, or Firm* — Young & Thompson

(57) ABSTRACT

The gripping device (1) enables the introduction and attachment of a set screw (101) within a U-shaped link connector (102) of a polyaxial or monoaxial pedicle screw (103) to immobilize a connecting rod (104) of a osteosynthesis device (100), and includes a locking element (2) which is supported against the link connector (102) making it possible to ensure concentricity between the principal axes of the gripping device (1) and those of the link connector (102) and to ensure that the connecting rod (104) is kept on the inside of the link connector (102); and an element for releasing (3) the gripping device (1) after establishing and screwing the set screws (101) inside the link connector (102).

10 Claims, 16 Drawing Sheets

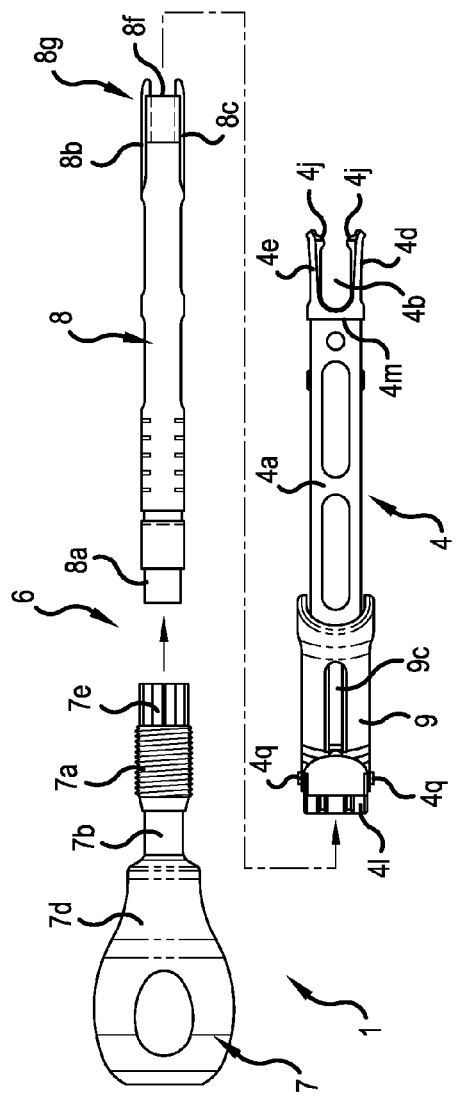

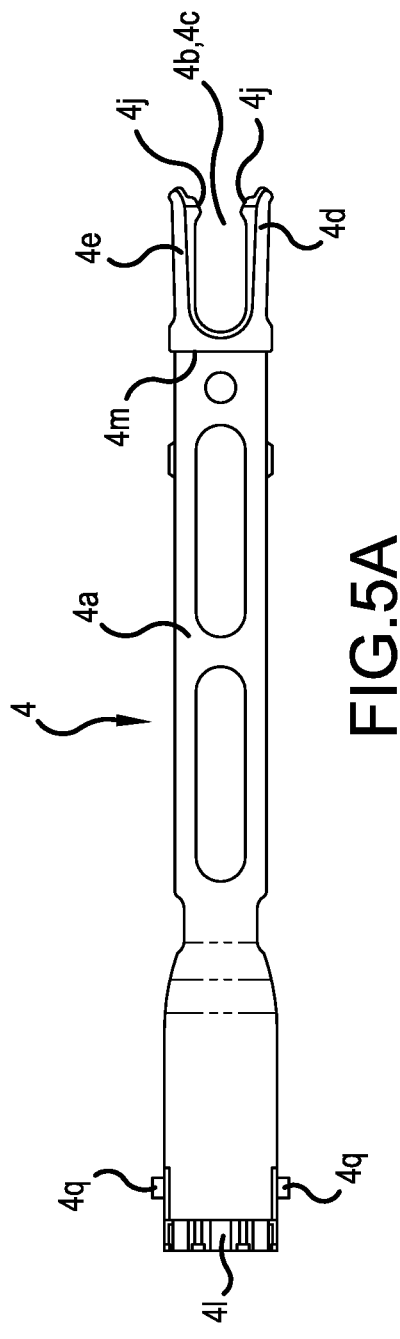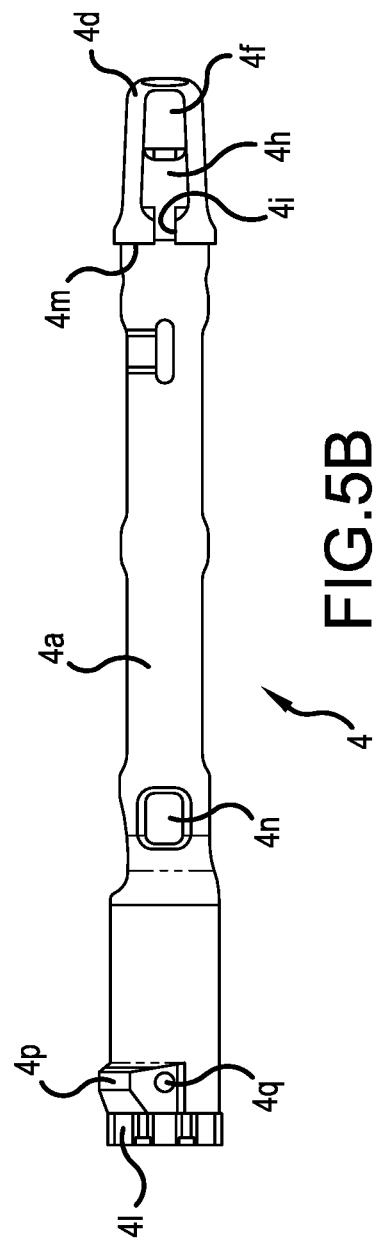

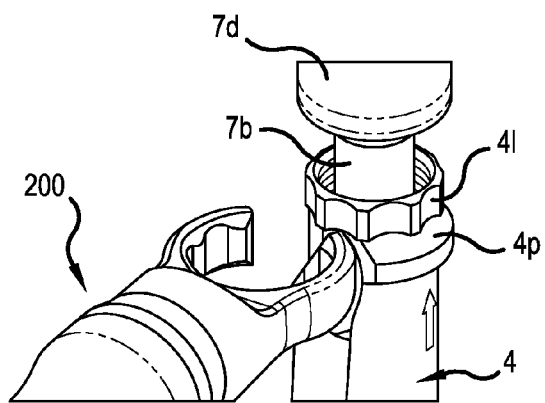
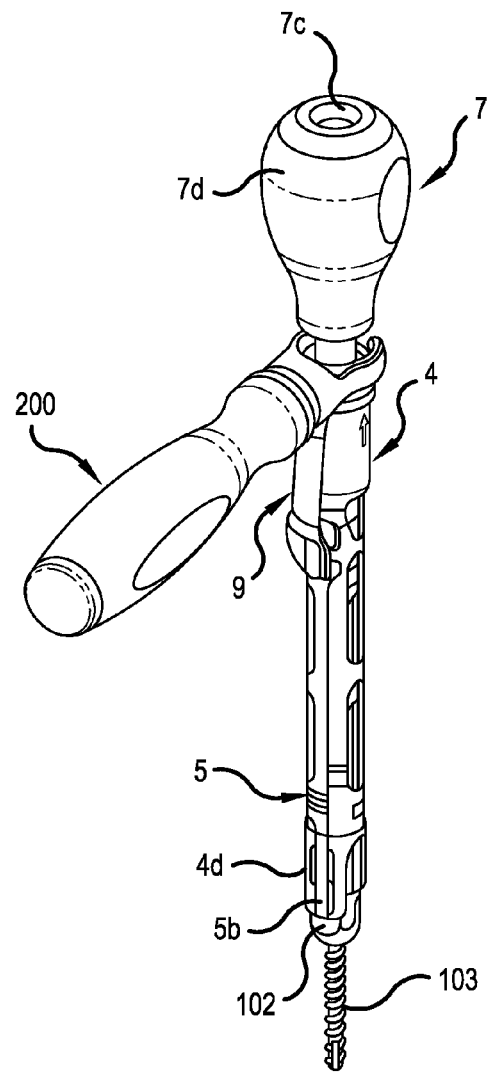
FIG.10A
FIG.10B

GRIPPING DEVICE FOR A PEDICLE SCREW

FIELD OF THE INVENTION

This invention relates to a gripping device enabling the introduction and attachment of a set screw within a U-shaped link connector of a polyaxial or monoaxial pedicle screw to prevent rotation and translation of a connecting rod of an osteosynthesis device which is known per se.

BACKGROUND OF THE INVENTION

Gripping devices of this type are known which allow set screws to be introduced inside a link connector to immobilize a connecting rod.

For example, we note that the gripping devices most known per se and described in prior patents US2004/0049191 and WO2008039441 teaches the attachment of a link connector by means of a hinge system or an elastic deformation device. These solutions do not facilitate a good grip on the link connector, spontaneously and frequently undipping, nor do they make an easy release possible, an inability to extract said link connector due to interference from the flesh, for example.

Earlier gripping devices do not allow one to adjust and ensure alignment between the main axes of the device and those of the link connector built into the pedide screw.

This condition requiring adjustment of the alignment, is indispensable to make the gripping device practical to use and to limit the patients risk of a bad attachment of the connecting rod into the link connector of the osteosynthesis device known per se.

The gripping device in accordance with this invention, enables the introduction and attachment of a set screw within a U-shaped link connector of a polyaxial or monoaxial pedide screw to immobilize a connecting rod of an osteosynthesis device which is known per se.

SUMMARY OF THE INVENTION

The gripping device in accordance with this invention comprises:
A means for locking which is supported against the link connector making it possible to ensure alignment between the principal axes of said gripping device and those of the link connector and to ensure that the connecting rod is kept on the inside of said link connector;
And a means for releasing the gripping device after establishing and screwing the set screws inside the link connector.

The gripping device according to this invention comprises a means for locking which consists of:
a guide body ensuing the placement of said gripping device around the link connector of the pedide screw;
a sleeve with flexible tabs having a shortened profile for assembling around the guide body;
and a means of translation constituting a guide handle which operates, first, via a double threaded link to the guide body and, secondly, by means of a pivot connection with a tube that pushes a guided rod to the inside and with respect to said guide body of said gripping device, in order to drive the connecting rod to the inside of the link connector and to have it rest upon the upper peripheral edge of said connector, said means of translation makes it possible to generate pressure force between said link connector and said tube which pushes the rod causing a displacement of the guide body so that it abuts against the flexible tabs of said sleeve having a suitable angle to block the inside space arranged inside the link connector.

The gripping device according to this invention includes a means for release (unlocking) which is constituted by a lever that provides guided rotation relative to the guide body, making it possible, after the release of the translational means, to exert translational force on the sleeve to the flexible tabs so as to move the latter with respect to said guide body causing separation of the flexible tabs and the release of said gripping device from the link connector.

The gripping device according to this invention comprises a guide body which is formed from a longitudinal tube comprising a first end provided with two lateral and opposite recesses defining two retaining branches in which the guide slots are arranged and a second end comprising an internal thread which works with the external one on a guiding handle.

The gripping device in accordance with this invention, comprises a guide body comprising on its external surface and between its two ends, a retaining means to introduce and attach the sleeve having flexible tabs so that the ends of said flexible tabs open into the guide slots of each retaining branch.

The gripping device according to this invention comprises a guide body comprising a linking means on the second end which works with those of the lever with the means of release allowing the latter to turn around said body and to then exert a translational force on the sleeve with flexible tabs so as to move the latter with respect to said guide body.

The gripping device according to this invention comprises a tube to push the rod of the translation means having a first end which works with the guide handle and a second end comprising two opposing projections, each having a concave shaped seat intended to work with the connecting rod of the osteosynthesis device in order to allow centering of the latter within the link connector.

The gripping device according to this invention comprises a push tube for a rod, the projections of which respectively comprising an external profile making it possible for angular indexing of said tube to push the rod inside of the guide body so that the concave shaped seat is always positioned in the lateral recesses of said guide body to allow passage of the connecting rod of the osteosynthesis device.

The gripping device according to this invention comprises a push tube for the rod comprising at the projections, a stop making it possible, when tightening the gripping device to ensure alignment of the principal axes of the link connector with those of said gripping device.

BRIEF DESCRIPTION OF THE DRAWINGS

The description that follows with regard to the attached drawings, given as non-limiting examples, will make it possible to better understand the invention, the characteristics which it presents and the advantages which are likely to be obtained:

FIGS. 1 and 2 are exploded views in perspective that illustrate the different elements constituting the gripping device according to this invention.

FIGS. 5A to 5D are side and cross sectional views showing the guide body of the gripping device according to this invention.

FIGS. 10A and 10B are views in perspective illustrating the introduction of a counter-torque device that works with the gripping device to ensure the tightening of the set screw of the osteosynthesis device.

DESCRIPTION OF THE INVENTION

Figure 3:
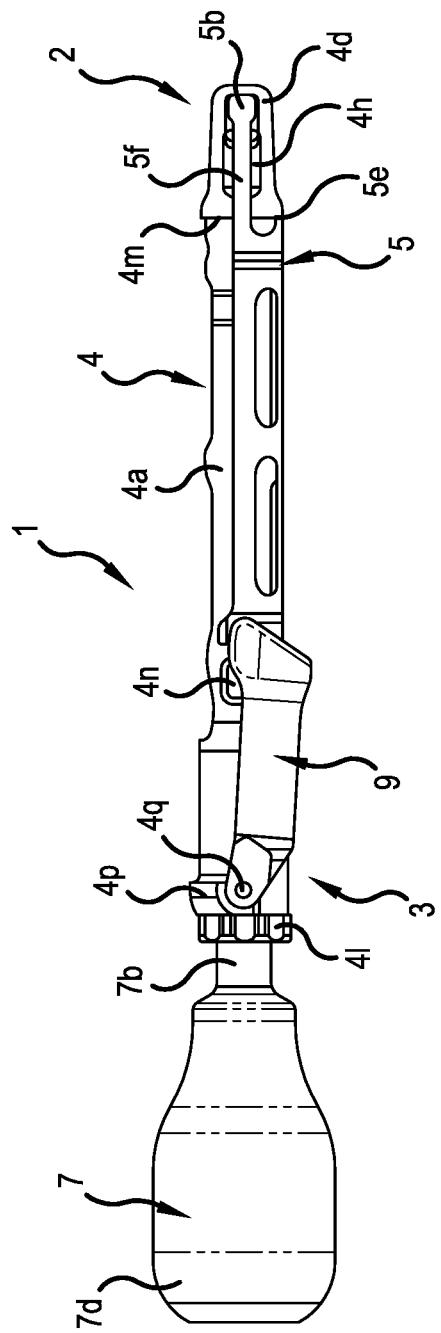
FIGS. 3 and 4 are side views showing the gripping device according to this invention in its assembled position.
Figure 4:
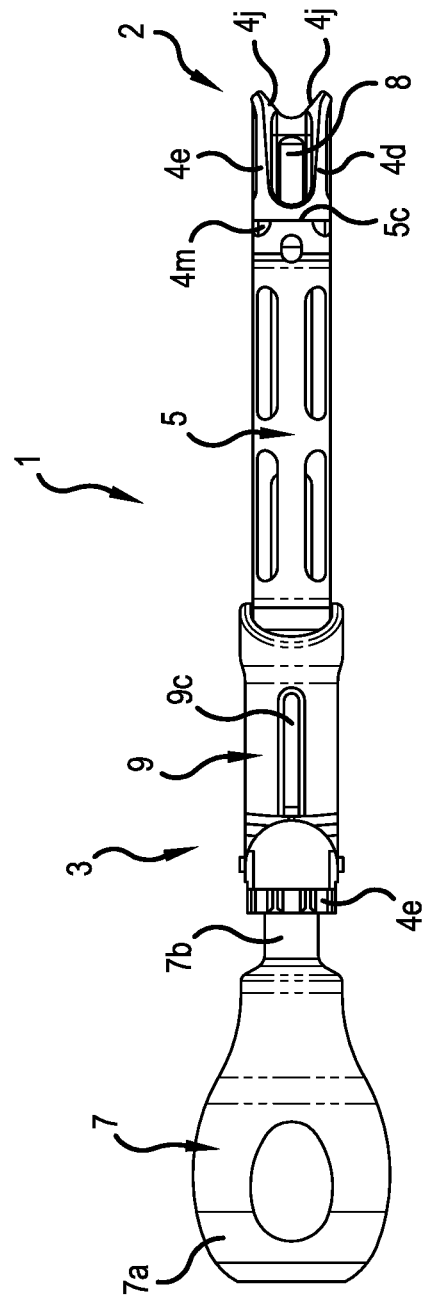

FIGS. 1 to 4 and 11 show a gripping device 1 comprising a means for locking 2 and a means for release 3 making it possible to introduce and tighten a set screw 101 on the inside of a U-shaped link connector 102 of a polyaxial or monoaxial pedicle screw 103 to immobilize a link rod 104 to prevent its translation and rotation on an osteosynthesis device known per se.

The means for locking 2 of the gripping device 1 is designed to be supported on the link connector 102 in order to ensure alignment of the principal axes of said gripping device 1 with those of said link connector 102 and also to maintain its immobilization with respect to the connecting rod 104 within and near the bottom of the U-link connector.

The means for release 3 makes it possible, after tightening the set screw 101 on the inside of the link connector 102 and locking the connecting rod 104 against rotating or translating in the bottom of the U, to release the locking means 2 and to release the gripping device 1 from the link connector 102 of the pedide screw 103 known per se.

The means for locking 2 is constituted by a guide body 4 to ensure the establishment of the gripping device 1 around the link connector 102 of the pedide screw 103, of a sleeve 5 with flexible tabs 5a, 5b and a means for translation 6.

FIGS. 5A to 5D, the guide body 4 of the means for locking 2 is shown, in a lengthwise profile of the tube 4a comprising a first end provided with two lateral and opposing recesses 4b, 4c opening to the outside to provide the passage of the connecting rod 104 and delimiting two retaining branches 4d, 4e in which the guide slots are respectively arranged 4f, 4g.

The external surface of each branch 4d, 4e and in the projection of the guide slots 4f, 4g comprises a flat edge 4h opening into a groove 4i making it possible to guide the flexible tabs 5a, 5b corresponding to the sleeve 5, when it is mounted around said guide body 4.

The inner surface of each branch 4d, 4e comprises a spur 4j having a dual-slope profile enabling locking and releasing the flexible tabs 5a, 5b corresponding to the sleeve 5 when the latter comes into contact with the link connector 102.

The longitudinal tube 4a comprises, opposite the first end, a second end comprising in its interior a threading 4k that works with that 7a of a guide handle 7 for the means of translation 6.

The outer surface and the second end of the longitudinal tube 4a comprises a cavity form 4l which couples with a handling tool 200 ensuring a counter torque device during the final tightening of the set screw 101 by means of an input device 300 (10A, 10B and 11).

Between the two ends of the longitudinal tube 4a, an external diameter is comprised which is smaller than that of said ends for receiving the sleeve 5 with the flexible tabs whose outer diameter is trimmed above the axis to ensure securing the assembly and the translation guide of said sleeve around said tube.

Figure 5C:
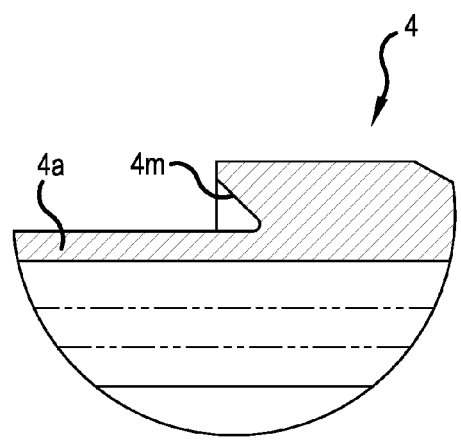
Figure 5D:
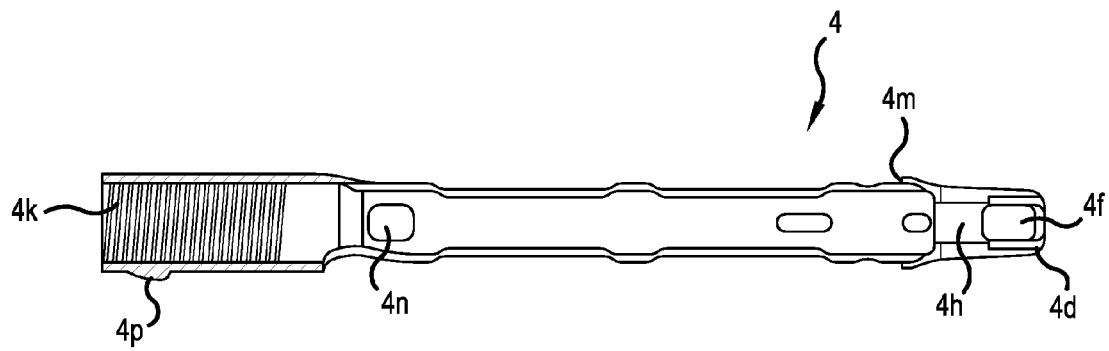
Figure 7A:
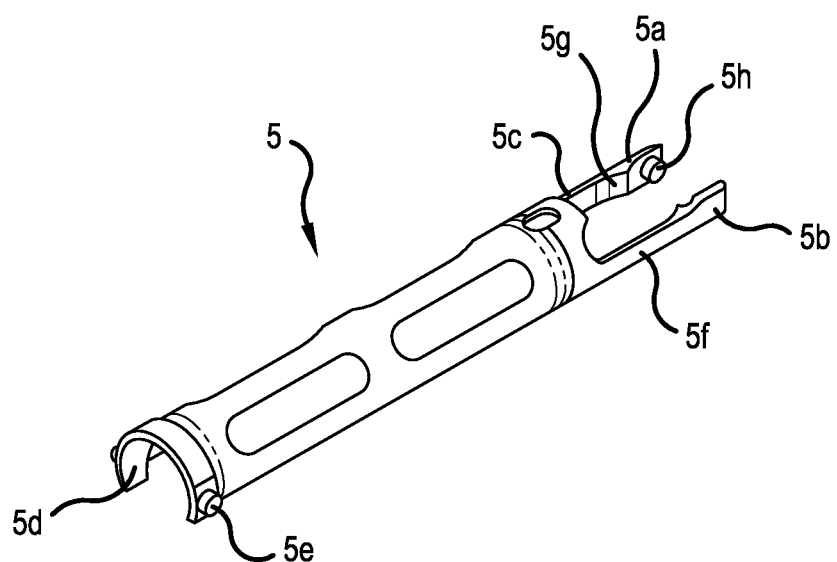
FIGS. 7A to 7B are side views and in perspective showing the sleeve with the flexible tabs of the gripping device according to this invention.
Figure 7B:
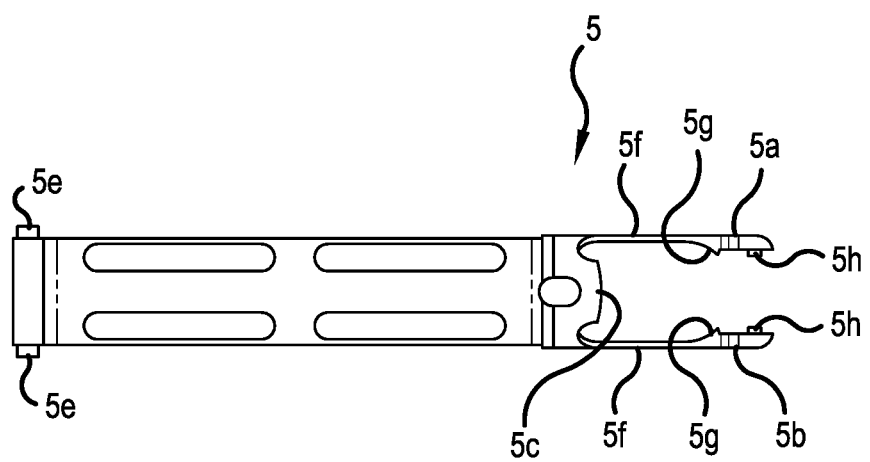

To do this, near the first end of the longitudinal tube 4a, there is a circular abutment 4m having a beveled profile which works with a stop 5c having a complementary profile arranged between the flexible tabs 5a, 5b of the sleeve 5 (FIGS. 5C, 7A and 7B).

Also, on the reduced portion thereof and opposite to the circular abutment 4m, the longitudinal tube 4a is provided with oblong openings 4n which are diametrically opposed to allow reception of the internal ribs 5d positioned opposite the flexible tabs 5a, 5b and exits the trimmed profile of the sleeve 5 (FIGS. 5B, 7A).

Figure 6A:
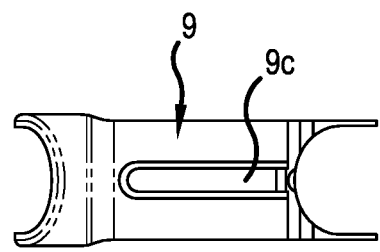
FIGS. 6A to 6C are side views and in perspective illustrating the lever with the release means of the gripping device according to this invention.
Figure 6B:
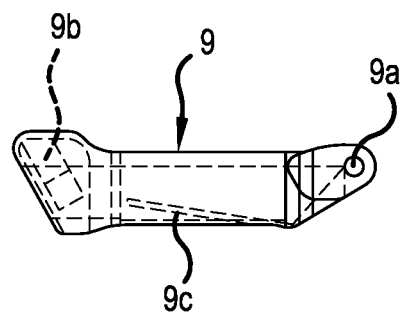
Figure 6C:
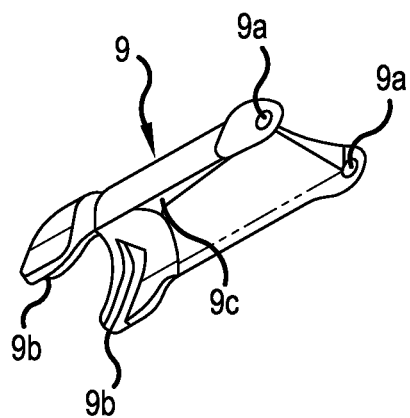

Close to the cavity form 4l, the longitudinal tube 4a comprises a semicircular rib 4p carrying at each end of the pins 4q working respectively with the holes 9a arranged at one of the ends of a lever 9 of the means to release 3 so as to a pivotal connection between said lever and the guide body 4 (FIGS. 5B, 6B and 6C).

In FIGS. 7A, 7B the sleeve 5 having flexible tabs 5d is shown, with guide axes 5e external ribs on the outer surface which respectively work with an indined and through-fitted groove 9b arranged in the inner part of the release lever 9 and opposite the holes 9a to convert the rotational movement of said lever 9 around the guide body 4 into a translational movement of said sleeve 5 along said guide body.

The release lever 9 comprises a lamella 9c machined from the body and plastically deformed towards the interior of said lever to form a return spring between the guide body 4 and the release lever 9 (FIGS. 6A and 6B).

Figure 11:
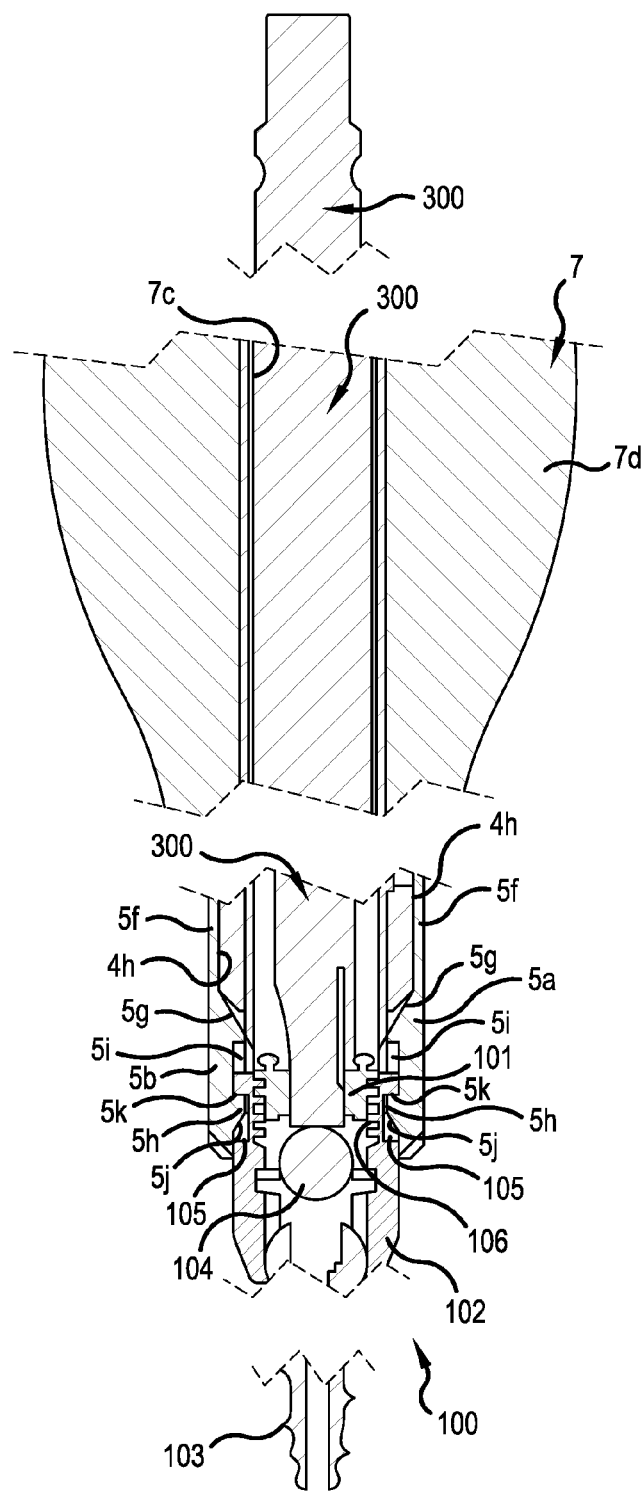
FIG. 11 is a cross-sectional view showing the set up of a device to insert the set screw inside the gripping device according to this invention.

The sleeve 5 comprises in the projection of its trimmed profile and opposite the guide axes 5e, flexible tabs 5a, 5b which are each constituted of a flexible part 5f which flex and an inner profile comprising an inclined wedge 5g and a spur 5h separated by a receiving space 5i (FIGS. 7A, 7B and 11).

Each indined wedge 5g make it possible to separate the flexible tabs 5a, 5b when the gripping device 1 is released from the link connector 102 of the pedide screw 103 using the lever 9 with the release means 3.

Each spur 5h has an oriented chamfer 5j and a flat edge 5k respectively ensure the insertion and maintenance during translation of the flexible tabs 5a and 5b to inside of the blind holes 105 implemented on both sides of the link connector 102 of the pedicle screw 103 known per se.

Figure 8A:
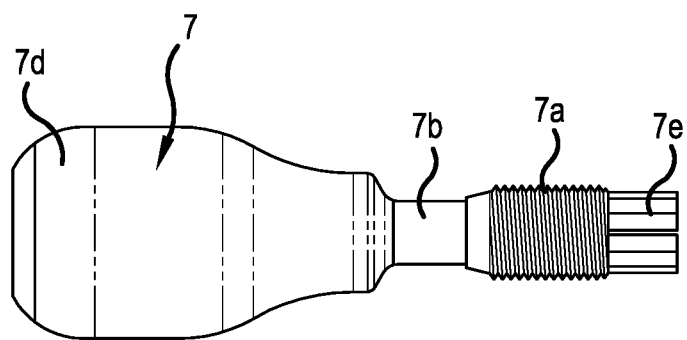
FIGS. 8A and 8B are side views showing the guide handle with the translating means of the gripping device according to this invention.
Figure 8B:
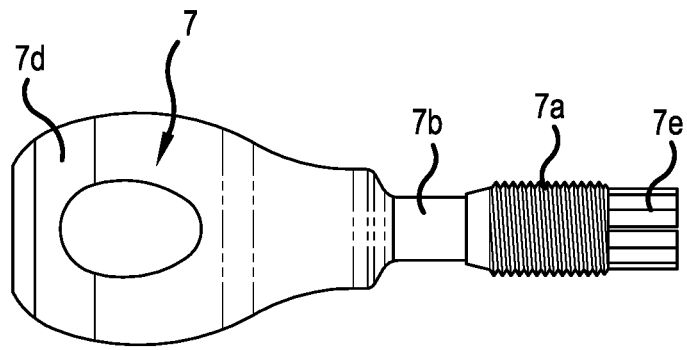

In FIGS. 8A, 8B and 10B the guide handle 7 of the translation means 6 is shown which consists of a cylindrical tube 7b perforated throughout by internal boring 7c for the passage and guidance of an input device 300 carrying the set screw 101 of the osteosynthesis device 100 known per se.

The cylindrical tube 7b comprises a gripping knob 7d built into one of its ends ensuring the surgeon has a perfect grip on the translation means 6.

The outer surface of the cylindrical tube 7b is machined to have a right handed double thread 7a enabling the conversion of the rotational movement into a translational movement when the surgeon uses the guide handle 7.

The cylindrical tube 7b comprises an projection of the double thread 7a; a quick coupling device constituted by flexible tabs 7e regularly distributed around the periphery of said tube and a rotary knob housed within the cylindrical tube 7b and for performing the pivot connection with the push tube for the rod 8.

Figure 9A:
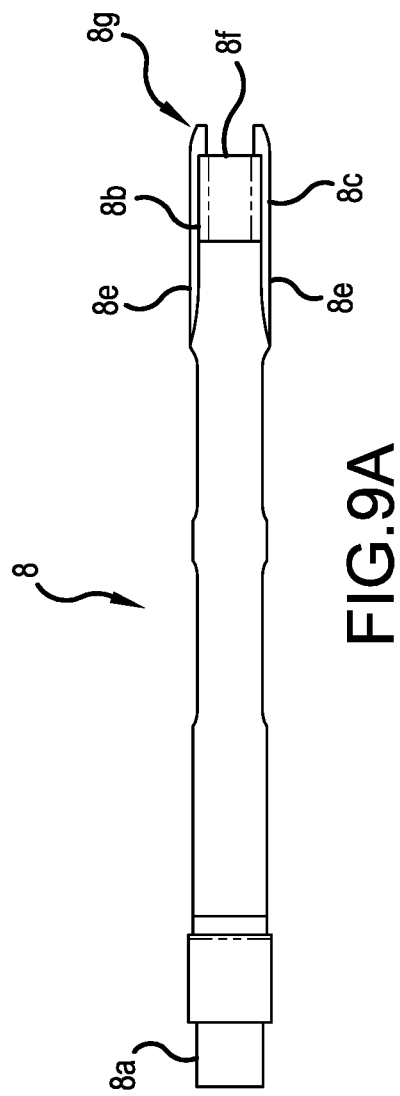
FIGS. 9A and 9B are side views illustrating the push tube for the rod of the translation means of the gripping device according to this invention.
Figure 9B:
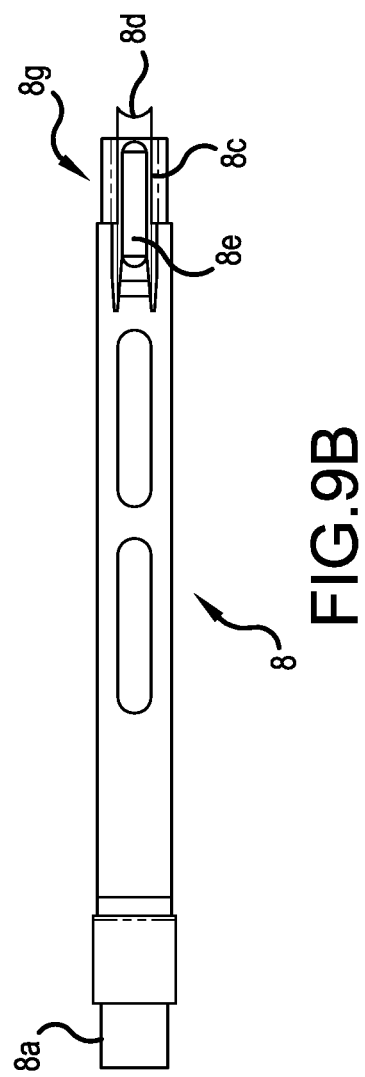

In FIGS. 9A and 9B the push tube for the rod 8 of the translation means 6 is shown that comprises a first end 8a of a cylindrical form and complementary to that of the coupling device with flexible tabs 7e and a rotary knob so as to work with the cylindrical tube 7b of the guide handle 7.

The push tube for the rod 8 comprises a second end 8g constituted of two opposing projections 8b, 8c each presenting a concave seat 8d designed to work with the connecting rod 104 of the osteosynthesis device 100 known per se in order to allow centering of the latter within the link connector 102.

The projections 8b, 8c of the push tube for the rod 8 respectively comprise an outer profile 8e that work with a complementary form arranged on the inside of the guide body to make angular indexing possible for said tube to push the rod inside the guide body 4.

This angular indexing of said push rod 8 relative to the guide body 4 makes it possible for the concave seat 8d to always be positioned in the lateral recesses 4b, 4c of said guide body 4 to make the passage possible of the connecting rod 104 of the osteosynthesis device 100 known per se.

At projections 8b, 8c of the push tube for the rod 8, there is a stop 8f which stops the action when tightening with the gripping device 1 the pedicle screw 103 rests on top of the link connector 102 so as to ensure alignment of the principal axes of said link connector 102 with those of said gripping device (FIGS. 9A and 11).

This alignment between the principal axes of the link connector 102 and the gripping device 1 makes it possible to correctly position the set screw 101 before its introduction and before it will work with the internal threading 106 of the link connector 102 (FIG. 11).

FUNCTIONING OF THE INVENTION

In FIGS. 12A to 12D, the release channel of the gripping device 1 is shown on the link connector 102 of the pedicle screw 103 known per se.

The polyaxial or monoaxial pedicle screw 103 provided with a link connector 102 must be first anchored in the pedicle of the Pv vertebra of a spinal segment of a spinal column to be fitted with the osteosynthesis device 100 known per se. The connecting rod 104 must also be presented above the link connector 102.

The surgeon presents and approaches the gripping device 1 so that the retaining branches 4d, 4e of the guide body 4 are resting against the upper edge of the U-shaped branches of the link connector 102.

In this position, one notes that the recesses 4b, 4c of the guide body 4 are within the projection of the openings of the U-shaped connector 102 to allow for the passage of the connecting rod 104.

The surgeon then bears down on the gripping device 1 guided along the U-shaped link connector 102. In this way, the flexible tabs 5a, 5b of the sleeve 5 deform around the link connector 102 by clipping into the blind holes 105 of the link connector. The gripping device 1 is then fixed onto the link connector 102 of the pedicle screw 103.

Figure 12A:
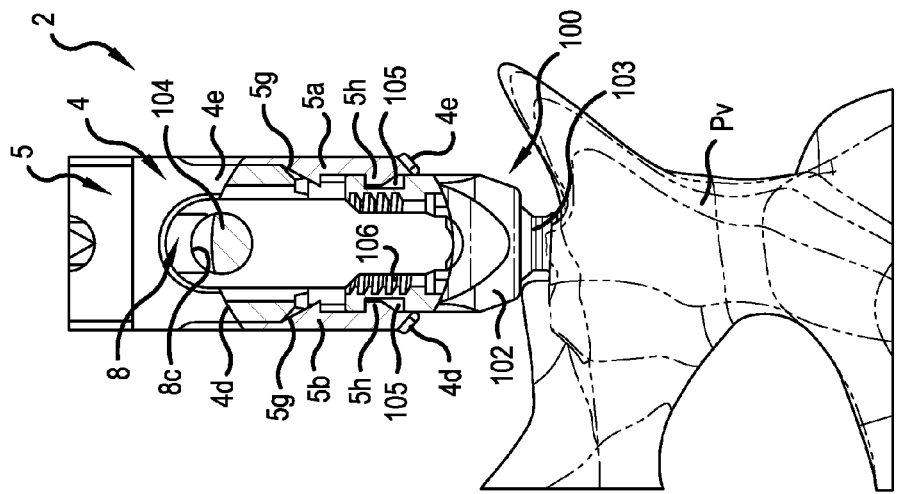
FIGS. 12A to 12D are cross-sectional views showing the various stages of the release channel of the gripping device on a link connector of a polyaxial pedide screw of an osteosynthesis device known per se.
Figure 12B:
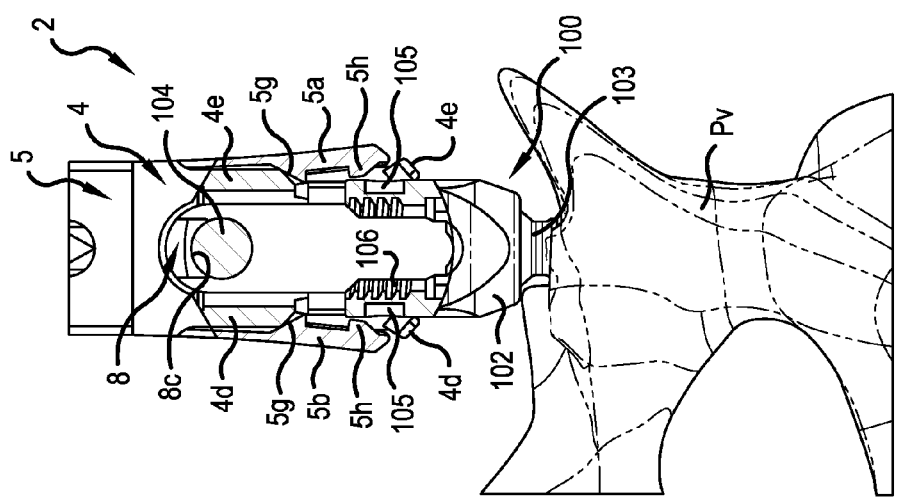
Figure 12D:
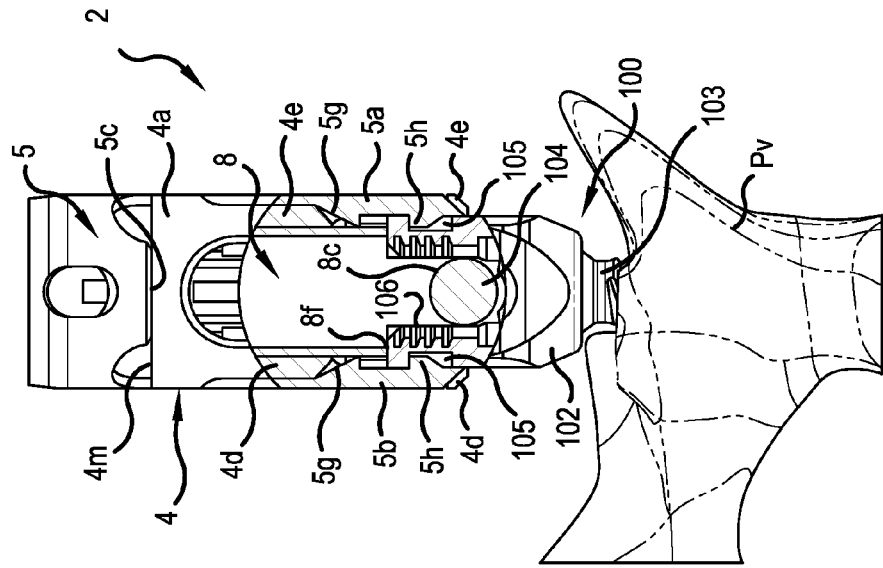
Figure 12C:
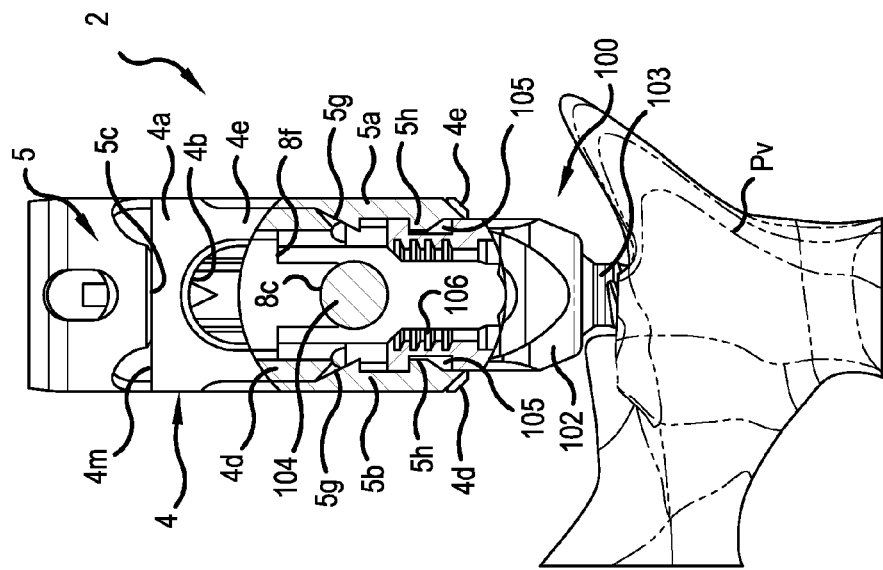
Figure 13B:
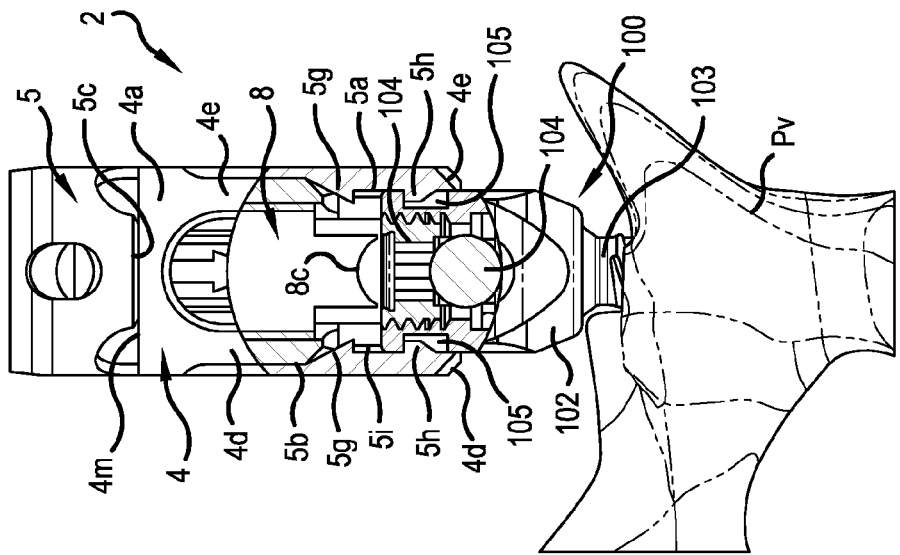
FIGS. 13A to 13D are cross-sectional views showing the various stages of the release channel of the gripping device of the link connector of a polyaxial pedide screw of an osteosynthesis device known per se.
Figure 13A:
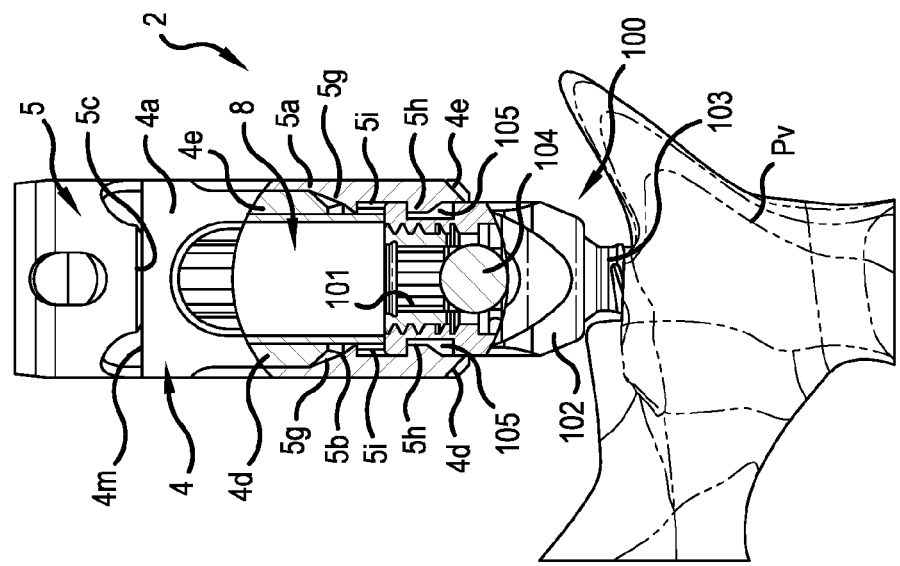
Figure 13D:
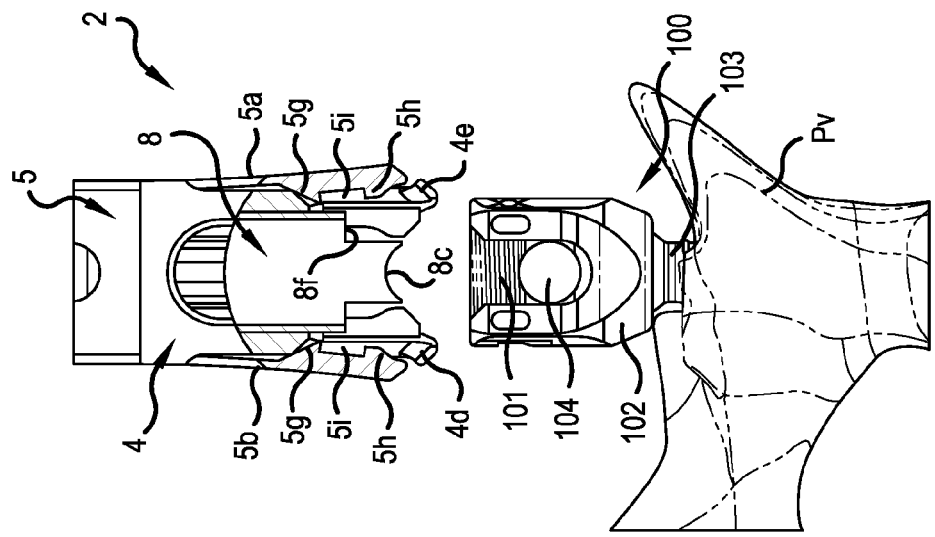
Figure 13C:
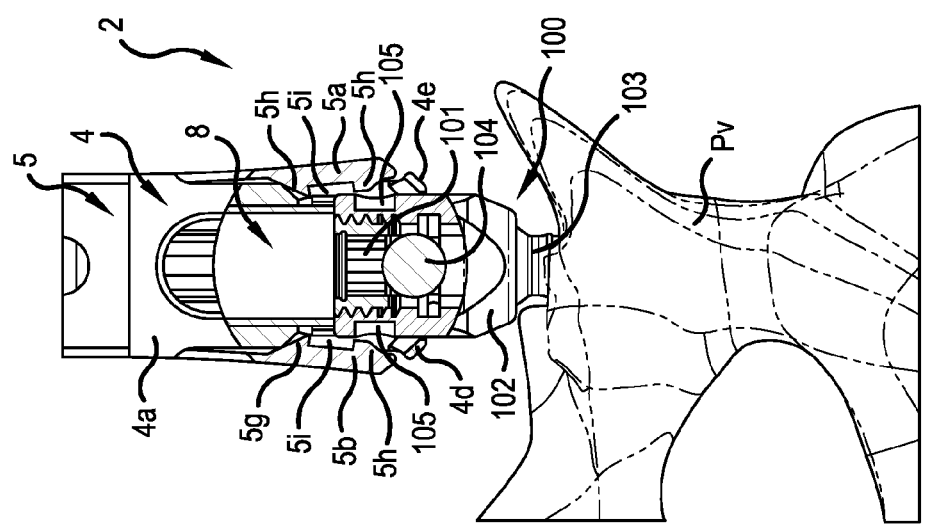

Then the surgeon actuates the knob 7d of the guide handle 7 in order to move the push tube for the rod 8 with respect to the guide body 4 and thus with regard to the link connector 102 of the pedicle screw 103. The push tube for the rod 8 enters into contact with the connecting rod 104 due to its seats 8d and pushes the latter in a centered manner into the bottom of the U-shaped profile of the link connector 102 (FIGS. 12C and 12D).

When the push tube for the rod 8 comes into contact above the link connector 102, it is stopped. The force of the pressure between the push tube for the rod 8 and the top of the link connector 102 causes an adjustment to occur between the guide body 4 and said link connector 102 (FIG. 14).

Figure 14:
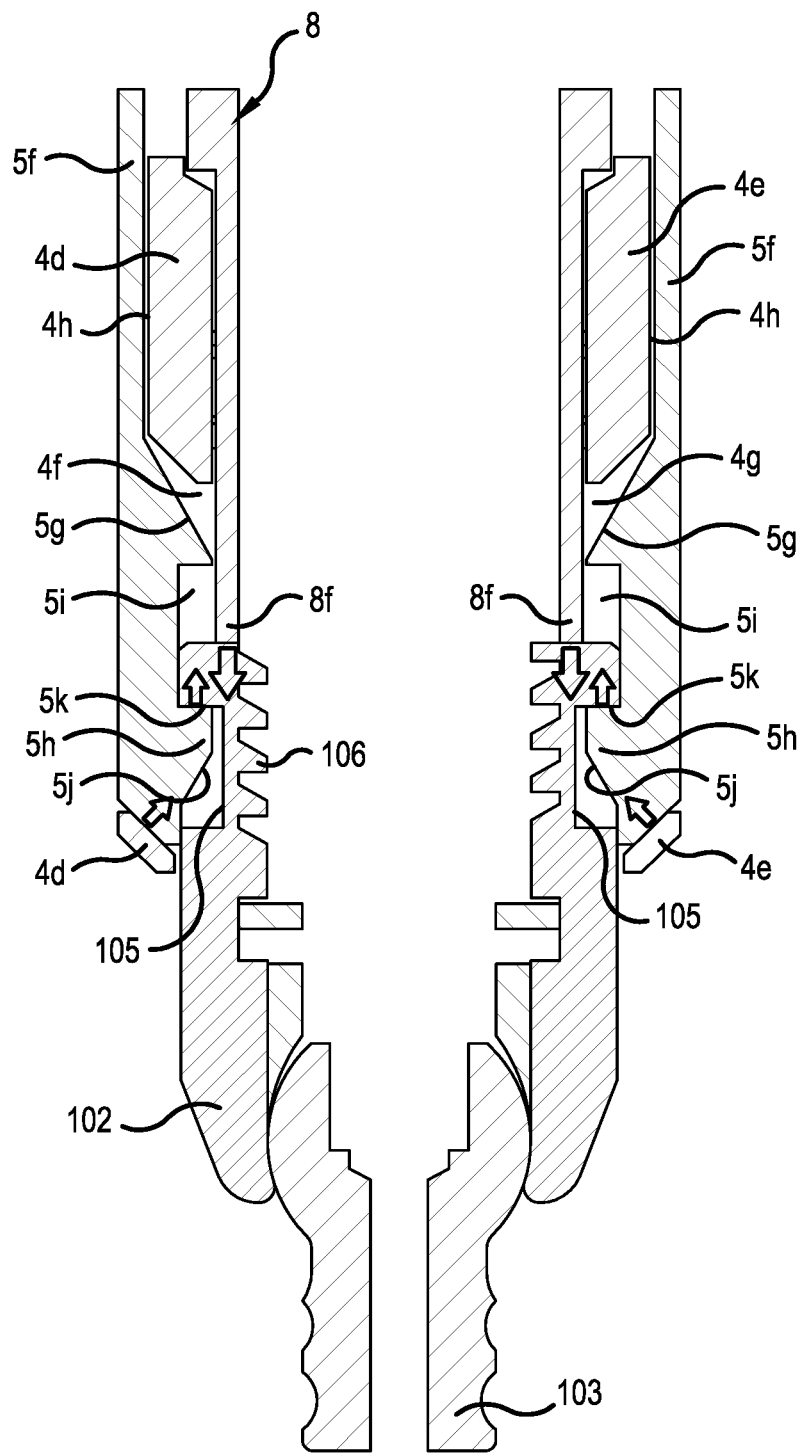
FIG. 14 is a detailed cross-sectional view showing the load and damping chain of the gripping device on the polyaxial pedide screw link connector of the osteosynthesis device known per se.

This adjustment makes it impossible for the flexible tabs 5a, 5b of the sleeve 5 to move apart because they are blocked by the ends of the retaining branches 4d, 4e of the guide body 4 (FIG. 14).

As soon as the push tube for the rod 8 is in abutment against the top of the link connector 102, the gripping device 1 is completely fixed and secured to said link connector 102 making the main axes of said gripping device 1 aligned with those of said link connector 102. The alignment of the main axes makes it possible to correctly position the set screw 101 by using the input device 300 in order for the latter to work with the internal threading 106 of the link connector 102 (FIGS. 12A to 12D and 14).

FIGS. 13A to 13D show the release canal of the gripping device 1 of the link connector 102 of a pedicle screw 103 known per se.

The release of the gripping device 1 from the link connector 102 requires release of the pressure generated by said gripping device on said actuator connector in a direction that is the opposite of the action used with the knob 7d of the guide handle 7.

By moving the push tube for the rod 8 in a direction that is the opposite of the link connector 102, free game is set up between the guide body 4 and the flexible tabs 5a, 5b of the sleeve 5.

By actuating the release lever 9, the sleeve 5 with flexible tabs is moved in a direction opposite to the link connector 102 causing the flexible tabs 5a, 5b of the sleeve 5, to open as they are left free due to the play produced between them and the guide body 4.

The opening of the flexible tabs 5a, 5b of the sleeve 5 occurs due to the two inclined wedges 5g arranged on the internal surface of said flexible tabs that are up and along the guide body 4, respectively resting on the flat edges 4h of the retaining brandies 4d, 4e forcing them to move apart from the link connector 102.

Then the opening between the flexible tabs 5a, 5b is sufficient, the gripping device 1 is disconnected from the link connector 102 allowing it to be withdrawn.

It should be understood that the above description was given only as an example and by no means limits the field of the invention, nor will it be outside the field of the invention, if implementation details described are replaced with any other equivalent.

The invention claimed is:

1. A gripping device (1) enabling the introduction and attachment of a set screw (101) within a U-shaped link connector (102) of a polyaxial or monoaxial pedicle screw (103) to immobilize a connecting rod (104) of an osteosynthesis device (100), the gripping device comprising:
   a guide handle (7);
   a guide body (4) opening, at a first end, to an outside to provide a passage of the connecting rod (104);
   a threaded link between the guide handle (7) and a second end of the guide body (4);
   a push tube (8) located and guided inside the guide body (4);
   a sleeve (5) with flexible tabs (5a, 5b), the sleeve (5) being mounted around the guide body (4);
   a lever (9) connected to the second end of the guide body (4), the lever (9) forming a pivot connection with the guide body (4),
   wherein, with the lever (9) engaged and with the guide body (4) resting against an upper edge of branches of the link connector (102), a force of pressure on the guide handle deforms the flexible tabs (5a, 5b) of said sleeve (5) around the link connector (102) to clip into blind holes (105) of the link connector (102) thereby fixing the gripping device (1) onto the link connector (102), and actuation of the guide handle (7), via the threaded link, pushes the push tube (8) inside the guide body (4) into contact with the connecting rod (104) providing alignment between principal axes of said gripping device (1) and those of the link connector (102) and ensuring that the connecting rod (104) is kept inside of said link connector,
   wherein release of the lever (9) moves the sleeve (5) to cause the flexible tabs (5a, 5b) to open for release (3) the gripping device (1) from the link connector (102) after establishing and screwing the set screw (101) inside the link connector (102).

2. The gripping device (1) according to claim 1, wherein, the lever (9) provides guided rotation relative to the guide body (4), to exert translational force on the sleeve to the flexible bars (5) so as to move the flexible bars (5) with respect to said guide body (4), causing the flexible tabs (5a, 5b) to move apart and the release of said gripping device (1) from the link connector (102).

3. The gripping device (1) according to claim 1, wherein the guide body (4) is comprised of a longitudinal tube (4a) having i) first end provided with two lateral and opposite recesses (4b, 4c) defining two retaining branches (4d, 4e) in which guide slots (4f, 4g) are arranged and ii) a second end comprising an internal thread (4k),
   the guide handle (7) includes an external threading (7a),
   the threaded link is comprised of the external one (7a) of the guiding handle (7) and the internal thread (4k) of the second end of the longitudinal tube (4a).

4. The gripping device (1) in accordance with claim 3, wherein an external surface of the guide body (4) comprises between the first and second ends of the guide body (4), a retaining means for establishment and attachment of the sleeve so that ends of said flexible tabs (5a, 5b) open onto an inside of the guide slots (4f, 4g) of each retaining branch (4d, 4e).

5. The gripping device (1) in accordance with claim 2, wherein the second end of the guide body (4) comprises a connecting means the works with the lever (9) allowing the lever to tilt about said guide body and to exert a translational force on the sleeve (5) so as to move the sleeve (5) with respect to said guide body (4).

6. The gripping device (1) according to claim 1, wherein the push tube (8) comprises a first end (8a) which works with the guide handle (7) and a second end (8g) comprising two opposing projections (8b, 8c), each projections (8b, 8c) with a concave shape seat (8d) designed to work with the connecting rod (104) of the osteosynthesis device (100) allowing the connecting rod (104) to be centered on the inside of the link connector (102).

7. The gripping device (1) according to claim 6, wherein, the guide body (4) is comprised of a first end provided with two lateral recesses (4b, 4c) defining two retaining branches (4d, 4e) in which guide slots (4f, 4g) are arranged, and
   the projections (8b, 8c) of the push tube (8) each have an external profile (8e) for angular indexing said push tube (8) to the inside the guide body (4) so that the concave seat (8d) is always positioned in the lateral recesses (4b, 4c) of said guide body (4) to allow passage of the connecting rod (104) of the osteosynthesis device (100).

8. The gripping device in accordance with claim 6, wherein the push tube (8) is provided at the projections (8b, 8c) with a stop (8f) so that when tightening the gripping device (1) the alignment of the main axes of the link connector (102) with those said gripping device (1) will be ensured.

9. A gripping device (1) enabling the introduction and attachment of a set screw (101) within a U-shaped link connector (102) of a polyaxial or monoaxial pedicle screw (103) to immobilize a connecting rod (104) of an osteosynthesis device (100), the gripping device comprising:
   a guide handle (7);
   a guide body (4) comprised of longitudinal tube (4a) with
      i) a first end comprising lateral and opposing recesses (4b, 4c) opening to an outside to provide a passage of the connecting rod (104), the recesses (4b, 4c) delimiting retaining branches (4d, 4e) in which guide slots (4f, 4g) are arranged, and ii) an opposite, second end;
   a threaded link between the guide handle (7) and the second end of the longitudinal tube (4a);
   a push tube (8) located and guided inside the guide body (4);
   a sleeve (5) with flexible tabs (5a, 5b), the sleeve (5) being mounted around the guide body (4);
   a lever (9) connected to the second end of the guide body (4), the release lever (9) forming a pivot connection with the guide body (4),
   wherein, with the lever (9) engaged and with the retaining branches (4d, 4e) of the guide body (4) resting against an upper edge of branches of the link connector (102), a force of pressure on the guide handle deforms the flexible tabs (5a, 5b) of said sleeve (5) around the link connector (102) to clip into blind holes (105) of the link connector (102) thereby fixing the gripping device (1) onto the link connector (102), and actuation of the guide handle (7), via the threaded link and, pushes the push tube (8) inside the guide body (4) into contact with the connecting rod (104) providing alignment between principal axes of said gripping device (1) and those of the link connector (102) and ensuring that the connecting rod (104) is kept on the inside of said link connector, the guide handle, the guide body, and the push tube extending along the principal axis of the gripping device, wherein release of the lever (9) moves the sleeve (5) to cause the flexible tabs (5a, 5b) to open for release (3) the gripping device (1) from the link connector (102) after establishing and screwing the set screw (101) inside the link connector (102).

10. The gripping device in accordance with claim 9, the lever (9) provides guided rotation relative to the guide body (4), to exert translational force on the sleeve to the flexible bars (5) so as to move the flexible bars (5) with respect to said guide body (4), causing the flexible tabs (5a, 5b) to move apart and the release of said gripping device (1) from the link connector (102).

* * * * *